United States Patent [19]

Shimizu et al.

[11] 4,167,725

[45] Sep. 11, 1979

[54] DEW-SENSING HYGROSCOPIC ELEMENT

[75] Inventors: Hidetoshi Shimizu; Hidemasa Tamura; Yoshimi Makino, all of Yokohama, Japan

[73] Assignee: Sony Corporation, Tokyo, Japan

[21] Appl. No.: 821,913

[22] Filed: Aug. 4, 1977

[30] Foreign Application Priority Data

Jun. 30, 1977 [JP] Japan ............................ 52/78084

[51] Int. Cl.² .............................................. H01L 7/00
[52] U.S. Cl. ...................................... 338/35; 422/98
[58] Field of Search ................... 338/35; 73/73, 335; 252/194; 340/602; 23/232 E, 254 E

[56] References Cited

U.S. PATENT DOCUMENTS 2,937,524  5/1960  Gregor ........................... 338/35 X
3,295,088  12/1966  Smith ............................ 73/335 X

OTHER PUBLICATIONS

F. W. Dunmore, Journal of Research of the National Bureau of Standards, "An Improved Hygrometer," vol. 23, pp. 701-714, Dec. 1939.
Koso Kisho, No. 3, May. 1954, pp. 1-12.
Keiso, Sep. 1960, pp. 21-26.

Primary Examiner—C. L. Albritton
Attorney, Agent, or Firm—Hill, Van Santen, Steadman, Chiara & Simpson

[57] ABSTRACT

A dew-sensing hygroscopic element includes a pair of electrodes and a dew-sensing hygroscopic material arranged between the electrodes which detects dew by the change of impedance between the electrodes. The dew-sensing hygroscopic material comprises polyvinyl alcohol having a saponification equivalent of 20 to 65 as a base material and contains an organic electrolyte.

7 Claims, 6 Drawing Figures

DEW-SENSING HYGROSCOPIC ELEMENT

BACKGROUND OF THE INVENTION

1. Field of the Invention

This invention relates to a dew-sensing hygroscopic element, and more particularly to a dew-sensing hygroscopic element which has high water-resistance, can be easily manufactured and is difficult to deteriorate.

2. Prior Art

When water is dewed on the surface of a head drum in a video tape recorder (VTR), a running magnetic tape in contact with such surface tends to adhere to the surface of the head drum to be entwined round the head drum, so that the magnetic tape often cannot run in a stable condition. In order to detect the dew water (moisture) on the surface of the head drum, a humidity-sensitive element of an electrical hygrometer is attached to the surface of the head drum in a VTR. The impedance of the humidity-sensitive element changes with changes in humidity. When the humidity is above a predetermined level, the electric hygrometer signals an alarm.

Humidity-sensitive materials for electrical hygrometers are generally classified into semiconductive materials and hygroscopic high molecular weight materials.

Electrical hygrometers using hygroscopic high molecular weight materials are generally divided into two types. In the electrical hygrometers of one type, electrically-conductive particles are dispersed into hygroscopic high molecular weight materials. The hygroscopic high molecular weight materials swell with humidity and thereby change the distances between the electrically-conductive particles and thus change the electrical resistance thereof. In the electrical hygrometers of the other type, hygroscopic high molecular weight materials contain dissociation ions, and changes in electrical conductivity with changes in humidity occur so that humidity is detected by a change in the generated signal.

The following hygroscopic high molecular weight materials are disclosed as humidity-sensitive materials for electrical hygrometers:

A mixture of silver powder and resins of polyvinyl ester derivatives, such as polyvinyl butyral (Japanese Patent Publication (after acceptance) No. 29627/1968);

Graft-polymerides of acrylic acid chloride and polyamino-polyethylene glycol (Japanese Patent Publication (after acceptance) No. 18836/1970);

A film of metal oxide and carbon powder impregnated with polyvinyl acetate or cellulose acetate (Japanese Patent Publication (after acceptance) No. 27438/1972);

A mixture of carbon powder, polyoxyethylene and cellulose (Japanese Patent Publication (after acceptance) No. 38190/1974);

A mixture of calcium sulfate as a base material, and an inorganic salt and an aqueous solution containing high molecular weight compounds such as PVA (polyvinyl alcohol), as a binding agent (Japanese Patent Publication (after acceptance) No. 20275/1975);

A mixture of a chlorine-containing resin and a polyamide resin (Japanese Patent Publications (no examination) No. 82877/1973; No. 67684/1974; No. 67685/1974 and No. 20781/1975);

Sulfonated cross-linked polystyrene, coated with an inorganic salt solution (Japanese Patent Publications (no examination) No. 17780/1973 and No. 17781/1973); and A cross-linked film of hydrophilic resins, such as acrylic esters, methacrylate esters, polyvinyl alcohols, polyvinyl acetals, polyacrylamides, polyvinyl pyrrolidones, polyethylene oxides, polyethylene imines, hydroxyethyl cellulose or cellophane (Japanese Patent Publications (no examination) No. 134198/1975).

The hygroscopic high molecular weight compounds of the type into which electrically-conductive particles are dispersed, are disadvantageous in that they exhibit hysteresis and that the humidity indication thereof are unstable in high humidity, such as over a relative humidity of 90%.

On the other hand, the hygroscopic high molecular weight compounds of the other type containing dissociation ions therein exhibit little hysteresis and are more sensitive to humidity. For example, an electrical hygrometer is known in which 0.5 to 1% by weight of LiCl is added to PVA (polyvinyl alcohol) having a saponification equivalent of 80 to 90 (Japanese magazine "Koso Kisho", No. 3, May, 1954), and a Dunmore-type electrical hygrometer is known in which 0 to 2.2% by weight of LiCl is added to PVA having a saponification equivalent of 36 ("Journal of Research of the National Bureau of Standards" vol 123, page 701, 1939). In such electrical hygrometers, the electrical resistance-humidity response is substantially linear and changes in humidity are detected by changes in electric resistance.

However, in the above-described electrical hygrometer, the concentration of LiCl, as an inorganic electrolyte, has a great influence on the linearity of the electrical resistance-humidity response. The concentration of LiCl must be finely adjusted within a relatively narrow range. However, LiCl tends to migrate from the humidity-sensitive element. This fact results in a decrease of the desired concentration of LiCl, and therefore to an increase in the resistance of the humidity-sensitive element. The above-described electrical hygrometers do not adequately function in the presence of dew (moisture) for a normal electrical hygrometer. In these conventional electrical hygrometers, the humidity-sensitive film (PVA) tends to dissolve into water or to become fluid or to deform, at a relative humidity around 100%, namely, when water is dewed or precipitated on the humidity-sensitive film. In such instance, LiCl is apt to dissipate into the precipitated moisture. Accordingly, hygrometers using PVA containing LiCl lack resistance to water, so that they cannot be used as a dew-sensing element. In the conventional electrical hygrometer, water dew is positively prevented from adhering to the humidity-sensitive element.

In order to obtain a hygroscopic element resistive to water dew (i.e. liquid) which can be used as a dew-sensing element, it has been proposed that PVA-ammonium bichromate having a saponification equivalent of 100 be photo-cross-linked (photo-hardened) so as to become water-insoluble (Japanese Patent Publication (after acceptance) No. 20276/1975). In addition, polyvinyl cinnamic acid-PVA copolymers and vinyl acetate-ethylene copolymers are suggested as water-insoluble photosensitivity resins, in place of the above PVA-bichromate. However, a hygroscopic element formed from such polymerized materials has the disadvantages that it is complicated in manufacture, that the diffusion speed of water within such material is low, that the response time of such a material is long, that it is costly and that the $Cr^{6+}$ ion derived from ammonium bichromate gives rise to pollution.

SUMMARY OF THE INVENTION

An object of this invention is to provide a dew-sensing hygroscopic element which has a high water-resistance property and is extremely suitable for detecting low dew (moisture).

Another object of this invention is to provide a dew-sensing hygroscopic element which has a relatively short response time and a relatively high stability.

A further object of this invention is to provide a dew-sensing hygroscopic element which can be simply manufactured without fear of pollution and without requiring complicated polymerization or cross-linking process.

In accordance with one aspect of this invention, a dew-sensing hygroscopic element includes a pair of electrodes and a dew-sensing hygroscopic material arranged between the electrodes, so that detection of dew occurs with a change of impedance between the electrodes. In accordance with the principles of the invention, the dew-sensing hygroscopic material within such dew-sensing element is comprised of polyvinyl alcohol having a saponification degree or equivalent ranging from 20 to 65 as a base material and contains therein an organic electrolyte.

The above and other objects, features and advantages of this invention, will be apparent in the following detailed description of illustrative embodiments which are to be read in connection with the accompanying drawings.

DESCRIPTION OF THE PREFERRED EMBODIMENTS

Polyvinyl alcohol according to one embodiment of this invention is produced by saponification (to a saponification equivalent of 20 to 65) of, for example, polyvinyl acetate, and has the following chain structure in which some hydroxyl groups, (—OH), are substituted by acetic groups, (—O—COCH$_3$).

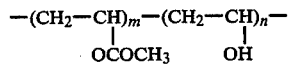

wherein n and m are numerals. As is known, the saponification equivalent can be readily controlled by a controlled reaction time or by a controlled concentration of the alkaline utilized.

The mean or average degree of polymerization of polyvinyl alcohol usable in the practice of the invention is 200 to 3000, and preferably is 500 to 2000. A film of polyvinyl alcohol having a mean degree of polymerization less than 200 does not have a desirable hardness, while a polyvinyl alcohol having a mean degree of polymerization over 3000 is less soluble, i.e. it is difficult to form a uniform film with a coating of such highly polymerized polyvinyl alcohol.

Figure 1:
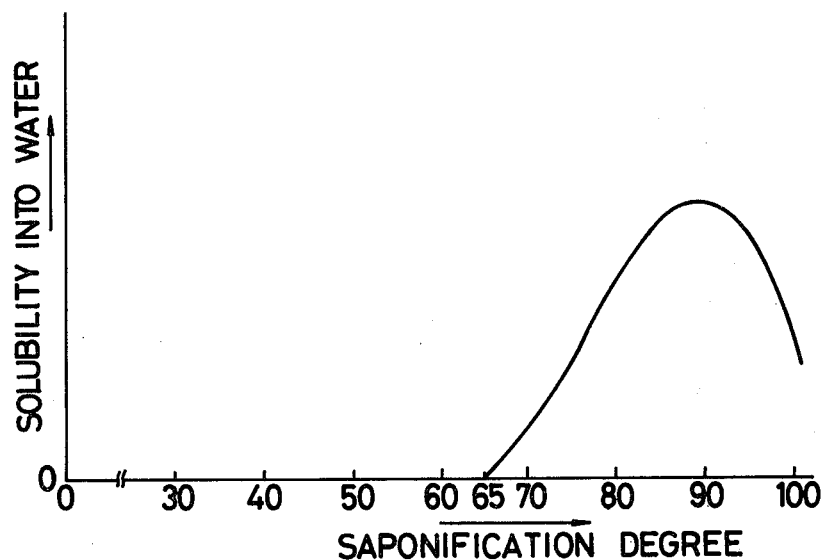
FIG. 1 is a graph illustrating the relationship between the saponification equivalent of polyvinyl alcohol and the solubility of polyvinyl alcohol into water.

The saponification degree or equivalent of polyvinyl alcohol is defined by:

$$\frac{n}{m+n} \times 100$$

wherein n and m are numerals, the sum of which ranges from 200 to 3000. When the saponification equivalent of a polyvinyl alcohol is low, namely, when the number of hydroxyl groups is relatively small, such polyvinyl alcohol is hard to dissolve in water. On the other hand, when the saponification equivalent of a polyvinyl alcohol is relatively high, namely, when the number of hydroxyl groups is relatively large, such polyvinyl alcohol is easily dissolved into water. FIG. 1 shows the relationship between the saponification degree or equivalent of polyvinyl alcohol and the solubility of polyvinyl alcohol into water. As apparent from FIG. 1, polyvinyl alcohol is soluble when the saponification equivalent is over 65. The solubility is at a maximum at a saponification equivalent of 90, and it is nearly zero when the saponification equivalent is less than 65, so that such polyvinyl alcohol is hardly soluble in water.

A reason why the saponification equivalent is limited to the range from 20 to 65 in accordance with the principles of the invention, is that the water resistance property of polyvinyl alcohol deteriorates due to some solubility thereof in water when the saponification equivalent is over 65. A saponification equivalent of 20 is a lower limit for hydrophilic polyvinyl alcohol because PVA having a lower saponification equivalent has an affinity for oil (i.e., such PVA become oleophilic) and water is hard to diffuse into such polyvinyl alcohol since the hygroscopic property thereof is deteriorated. Polyvinyl alcohol having a saponification equivalent in accordance with the principles of the invention, allow adequate diffusion of water, and, moreover, such polyvinyl alcohol is not dissolved in water. Polyvinyl alcohols having a saponification equivalent of 20 to 65 are a so-called, "low saponification" type polyvinyl alcohols.

A more preferable polyvinyl alcohol (PVA) is one having a saponification equivalent ranging from 30 to 60. Such polyvinyl alcohols are further superiod both in water resistance and in hygroscopic properties. Further, the closer the saponification equivalent of a polyvinyl alcohol is to 60, the more preferable that polyvinyl alcohol is.

It is very important to this invention that polyvinyl alcohol contain an organic electrolyte. In contrast to the hygroscopic high molecular weight compounds in which electrically-conductive particles are dispersed, the polyvinyl alcohol containing an organic electrolyte in accordance with the principles of the invention has the advantage that there is low hysteresis and such material is more sensitive to moisture. Organic electrolytes have a good affinity for polyvinyl alcohol, since they are also organic. No migration occurs between organic electrolytes and polyvinyl alcohol. Relatively small amounts of an organic electrolyte disperses into dew (liquified water) on the PVA film of the invention. Since the invention relates to a dew (liquid) sensing hygroscopic element but such element does not always require a linear humidity-resistance relation, as required with a conventional electrical hygrometer. Accordingly, the concentration of organic electrolyte does not need to be very strictly selected in accordance with the principles of the invention.

Next, the hygroscopic operating mechanism of dew-sensing hygroscopic materials according to the invention will be described.

In the operation mechanism, sodium acetate, ($CH_3COONa$), which is a reaction by-product remaining after the manufacturing process of the above described low saponification type polyvinyl alcohol, functions principally as an organic electrolyte.

A further amount of sodium acetate may, as occasion demands, be added into produced polyvinyl alcohol. The amount of sodium acetate remaining within PVA depends on the degree of purification utilized during the manufacturing process of polyvinyl alcohol. In an analysis of a polyvinyl alcohol used in an exemplary embodiment of the invention, the amount of by-product sodium acetate was about 0.03% by weight based on the total weight of PVA. When sodium hydroxide is used as the alkaline material during the saponification process, the so-produced low saponification type polyvinyl alcohol contains as a by-product, sodium acetate, which functions as an organic electrolyte in accordance with the principles of the invention. As may be obvious, when lithium hydroxide or potassium hydroxide, etc. is used as the alkaline material in the saponification process, the so-produced low saponification type polyvinyl alcohol contains, as a by-product, lithium acetate or potassium acetate etc. as the organic electrolyte. Clearly, lithium acetate and potassium acetate function equivalently to sodium acetate. In preferred embodiments of the invention, any additional organic electrolyte added to the by-product organic electrolyte (produced in situ during the synthesis of low saponification equivalent PVA) is the same as or equivalent to the by-product organic electrolyte. Preferably, the organic electrolyte to be added is an organic material selected from the group consisting of sodium salt, potassium salt or lithium salt of a $C_1$ to $C_{20}$ organic acid. Mono-, di- or tri-carboxylic organic acids having less than twenty carbon atoms may be used as the organic acids and fatty acids ($C_1$ to $C_5$) are preferred. Examples of useful mono-carboxylic organic acid, include saturated organic acid such as formic acid, acetic acid, propionic acid, ethylacetic acid, valeric acid, caproic acid, enanthic acid, caprylic acid, pelargonic acid, capric acid, undecylic acid, lauric acid, tridecylic acid, myristic acid, pentadecylic acid, palmitic acid, heptadecylic acid, stearic acid, nonadecanoic acid, arachic acid, and other similar mono-carboxylic organic acids and unsaturated organic acids, such as crotonic acid, isocrotonic acid, undecylenic acid, oleic acid, elaidic acid and other similar mono-carboxylic organic acids. Examples of useful di-carboxylic organic acid, include saturated di-carboxylic organic acids such as oxalic acid, malonic acid, succinic acid, glutaric acid, adipic acid, pimelic acid, suberic acid, azelaic acid, sebacic acid, etc., and unsaturated di-carboxylic organic acids, such as maleic acid, fumaric acid, etc. An example of a useful tri-carboxylic organic acid is citric acid. Besides the above-described alkali metal ions, any other metal can be used, as occasion demands, to form the cation of the organic electrolyte used in the practice of the invention. In any case, the radical of an organic acid, preferably fatty acid radical, is used as the anion of the organic electrolyte in the practice of the invention. A reason why organic acids having less than twenty carbon atoms are preferred for use in this invention, is that organic acids having more than twenty carbon atoms are hard to dissolve into water, and yield inferior dissociation effects.

According to the principles of the invention, the amount of organic electrolyte, for example, sodium acetate utilized with the low saponification type PVA is 0.05 to 10% by weight (based on the weight of PVA) and preferably 0.5 to 5% by weight. The amounts, 0.05 to 10% by weight and 0.5 to 5% by weight, correspond to about $6\times10^{-4}$ to 0.14 gram equivalent of the organic electrolyte, and $6\times10^{-3}$ to $6\times10^{-2}$ gram equivalent of the organic electrolyte, based on 100 grams of dew-sensing hygroscopic material, i.e., low saponification type PVA and the said electrolyte.

When the amount of organic electrolyte is too low, the dissociation effect is weak. When the amount of organic electrolyte is too large, an excess of the organic electrolyte exudes on the film, and a so-called "blooming" often occurs.

A small amount (by weight) of, for example, 10 PHR (parts by weight per 100 parts of PVA resin) of electrically conductive particles may also be added to the low saponification type (equivalent or degree) polyvinyl alcohol, besides the above described organic electrolyte. For example, Ag powder (having an average grain size of about 0.1 to $1\mu$), carbon black (having an average grain size of about 0.01 to $0.3\mu$), graphite (having an average grain size of about 10 to $100\mu$), glass beads (having an average grain size of about 10 to $100\mu$) and/or $TiO_2$ powder (having an average grain size of about 0.1 to $0.4\mu$) may be used as the electrically-conductive particles for this invention.

When water is dewed or precipitated on a PVA film of the dew-sensing hygroscopic material of the invention, water diffuses into such film very effectively and functions to electrolyticly dissociate the electrolyte. Preferably the dew-sensing hygroscopic material (i.e., PVA film with organic electrolyte therein) is a coating arranged between a pair of electrodes and has a thickness of about 2 to $9\mu$. Since the dew-sensing hygroscopic film in accordance with the principles of the invention is formed of non-cross-linked low saponification degree polyvinyl alcohol, such film has superior stability and has a higher diffusion rate for water, so that the response time is short.

In order to demonstrate the advantages of the invention, a polyvinyl alcohol having a saponification equivalent or degree of 55 (commercially available under the tradename "L-17", manufactured by the Nippon Synthetic Chemical Industry Co., Ltd., Japan) and a polyvinyl alcohol having a saponification degree of 36 (obtained from the Nippon Synthetic Chemical Industry Co., Ltd.) were used as sample materials to examine the stability to water and the response thereof to moisture. Both of these PVA materials had a mean degree of polymerization of about 1700. The amount of sodium acetate in the polyvinyl alcohol material having a saponification degree of 55 was 0.76% by weight, and the amount of sodium acetate in the sample polyvinyl alcohol having a saponification degree of 36 was 0.51% by weight. Films were formed in a conventional manner from these sample materials and analysis made, the results of which are tabulated in Table I below. The hygroscopic films formed from low saponification degree PVA, which were in contact with water for more than ten days, were stable and did not deteriorate. The reason seems to be that such low saponification polyvinyl alcohol does not dissolve in water and does not become fluid.

The Table I shows the pertinent hygroscopic properties. As apparent from the Table I, the equilibrium impedance of the hygroscopic film of this invention, after being sufficiently exposed to a predetermined humidity, is low in comparison with conventional hygroscopic film.

TABLE I

| Sample No. | 1 | 2 | 3 | 4 | 5 (for comparison) |
|---|---|---|---|---|---|
| Saponification degree | 55 | 55 | 55 | 36 | 90~100 |
| Solvent | methanol:water= 6:4 | methanol:water= 6:4 | methanol:water= 6:4 | Methanol | Water |
| Thickness of film | 3μ | 6μ | 9μ | 2μ | 10≈μ |
| Equilibrium impedance $Z_1$ | $8\times10^3\Omega$ | $1\times10^4\Omega$ | $7\times10^4\Omega$ | $7\times10^3\Omega$ | $7\times10^{4\sim5}\Omega$ |
| Equilibrium impedance $Z_2$ | | $10^3\Omega(\text{Initial})\sim3\times10^4\Omega(\text{Final})$ | | $7\times10^3\Omega$ | $7\times10^{3\sim4}\Omega$ |

As may be apparent, the solvent for the PVA material having a saponification equivalent or degree of 55 or less could not be only water because such low saponification PVA is insufficiently soluble in water, as is apparent from FIG. 1.

In the Table I, the sample Nos. 1 to 4 represent the hygroscopic films produced in accordance with the invention. Sample No. 5 represents a conventional hygroscopic film produced for comparison in such a manner that the polyvinyl alcohol thereof had a mean degree of polymerization of about 1700 and a saponification degree of 90 to 100 and was photo-cross-linked after addition of ammonium bichromate. The equilibrium impedance, $Z_1$, was measured at the temperature of 20° C., a relative humidity of 98% RH and at a frequency of 300 Hz. The equilibrium impedance $Z_2$ was measured when the hygroscopic film was brought into contact with water. Both of the equilibrium impedances, $Z_1$ and $Z_2$, are represented by absolute values. As apparent from the Table I, the equilibrium impedances $Z_1$ and $Z_2$ of the sample Nos. 1 to 4 are low, namely, the changes in the impedances in sample Nos. 1 to 4 are large, in comparison with those of sample No. 5. It is concluded from the results of the Table I that an organic electrolyte, such as sodium acetate, contributes greatly to the electrical conductivity of the hygroscopic film in the sample Nos. 1 to 4.

The Table II shows the results of response times in sample Nos. 1 to 5 which are the same as sample Nos. 1 to 5 of the Table I, respectively. Times required for the impedances of the respective samples to change from the initial impedance (higher than $10^7\Omega$) to $10^5$ were measured at the temperature of 22° C., a relative humidity of 98% RH and at a frequency of 300 Hz.

TABLE II

| Sample No. | 1 | 2 | 3 | 4 | 5 (for comparison) |
|---|---|---|---|---|---|
| Time | 35 sec. | 45 sec. | 270 sec. | 15 sec. | 720 sec. |

As can be deducted from the results shown in Table II, the response times of sample Nos. 1 to 4, produced in accordance with the invention, are much shorter than the response time of sample No. 5, which is a conventional hygroscopic film.

Figure 2:
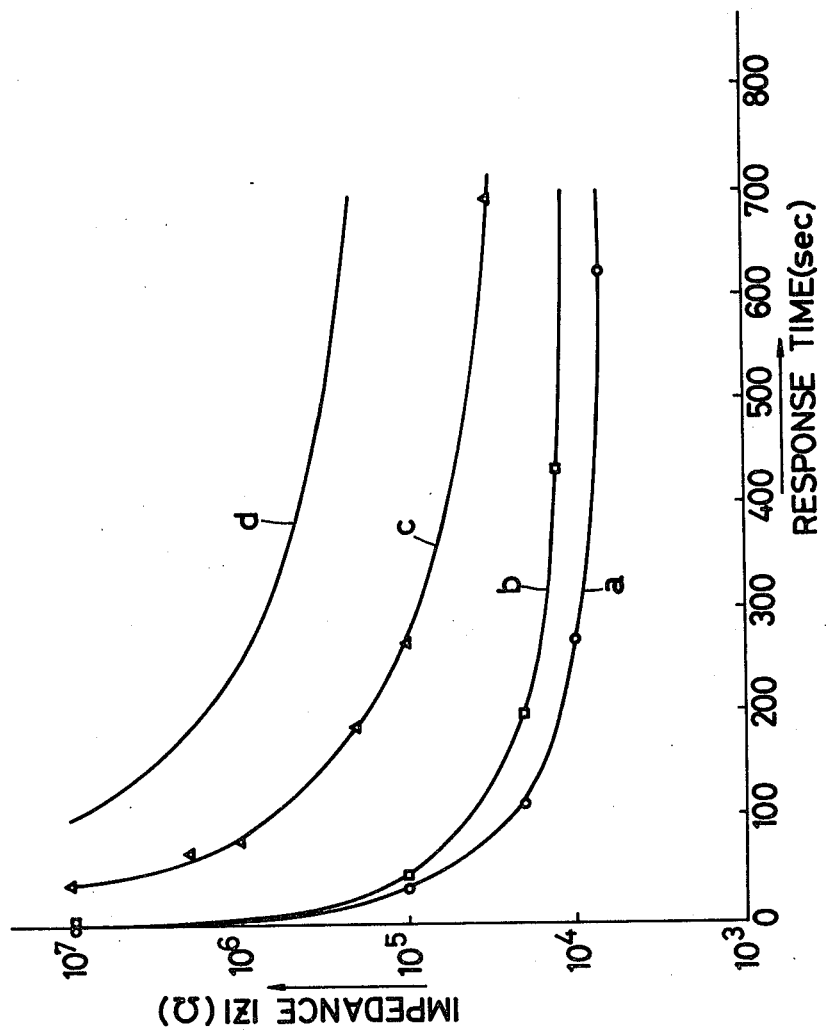
FIG. 2 is a comparison graph showing the relationships between the response time and the impedance.

FIG. 2 shows the various results of the response times. In FIG. 2, the ordinate axis represents the impedance (Z), and the abscissas axis represents the response time (in sec) while the films were in contact with moisture. The response times were measured at the frequency of 300 Hz in an atmosphere of 22° C. and 98% RH, into which atmosphere the samples were displaced from an atmosphere of 22° C. and 31% RH. The curve a shows data on sample No. 1, hygroscopic film (3μ thick), which was produced in accordance with the invention and was formed from a polyvinyl alcohol base material having a saponification equivalent or degree of 55 at the temperature of 100° C. by a coating operation of ten minutes. The curve b shows data on sample No. 2, hygroscopic film (6μ thick), which was produced in accordance with the invention and which was formed from a polyvinyl alcohol base material having a saponification degree of 55 at the temperature of 70° C. by a coating operation of thirty minutes. The curve c shows data on sample No. 3, hygroscopic film (9μ thick), produced in accordance with the invention and which was formed from a polyvinyl alcohol base material having a saponification degree of 55 at the temperature of 70° C. by the coating operation of thirty minutes. Curve d shows data on sample No. 5, conventional hygroscopic film, which was formed from a photo-cross-linked polyvinyl alcohol base material.

As apparent from FIG. 2, the response time (which is, for example, the time required for the impedance of a hygroscopic film to change from the initial impedance higher than $10^7\Omega$ to a reference impedance of $10^5\Omega$), of the sample films produced in accordance to the invention, is remarkably short in comparison with the response time of the conventional hygroscopic film. And the equilibrium impedance of the exemplary embodiments produced in accordance to the invention is lower than that of the conventional hygroscopic film.

For further demonstrations on the change of equilibrium impedance, demonstration sample hygroscopic films (5μ thick) were formed of a polyvinyl alcohol base material having a saponification degree or equivalent of 36, and which contained an organic electrolyte or an inorganic electrolyte at a constant 0.2 gram equivalent/liter concentration of metallic ions. The changes of the equilibrium impedance of these demonstration samples were measured at the temperature of 20° C., a relative himidity of 98% RH and at a frequency of 300 Hz, after contact with water for a predetermined time period. The results are shown in Table III, in which the sample Nos. 6 and 7 are the conventional hygroscopic films, and the sample Nos. 8 to 10 are the hygroscopic films produced in accordance with the invention.

TABLE III

| Sample No. | Electrolyte | Contact time (in water) | | | | | |
|---|---|---|---|---|---|---|---|
| | | 0 min. | 30 min. | 5 hours | 1 day | 10 days | 30 days |
| 6 | Lithium chloride | $\sim 10^4 \Omega$ | $\sim 10^5 \Omega$ | $\sim 10^6 \Omega$ | $> 10^7 \Omega$ | $> 10^7 \Omega$ | $> 10^7 \Omega$ |
| 7 | Ammonium bichromate | $\sim 10^4 \Omega$ | $\sim 10^5 \Omega$ | $\sim 10^6 \Omega$ | $> 10^7 \Omega$ | $> 10^7 \Omega$ | $> 10^7 \Omega$ |
| 8 | Sodium acetate | $\sim 10^4 \Omega$ | $\sim 10^4 \Omega$ | $\sim 10^4 \Omega$ | $\sim 10^4 \Omega$ | $10^4 \sim 10^5 \Omega$ | $10^4 \sim 10^5 \Omega$ |
| 9 | Sodium palmate | $\sim 10^4 \Omega$ | $\sim 10^4 \Omega$ | $\sim 10^4 \Omega$ | $\sim 10^4 \Omega$ | $10^4 \sim 10^5 \Omega$ | $10^4 \sim 10^5 \Omega$ |
| 10 | Sodium citrate | $\sim 10^4 \Omega$ | $\sim 10^4 \Omega$ | $\sim 10^4 \Omega$ | $\sim 10^4 \Omega$ | $10^4 \sim 10^5 \Omega$ | $10^4 \sim 10^5 \Omega$ |

As apparent from Table III, the conventional hygroscopic elements containing inorganic electrolyte cannot be used as a dew-sensing hygroscopic element, since the water resistance property thereof is severely deteriorated with prolonged contact time in water, namely the electrical resistance increases greatly with the contact time. On the other hand, organic electrolyte has a good affinity for polyvinyl alcohol, and a relatively small degree of migration of the organic electrolyte occurs due to contact with water in the dew-sensing hygroscopic elements constructed and operating in accordance with the invention (Sample Nos. 8 to 10). The dew-sensing hygroscopic elements according to this invention are stable and resistant to liquified water, so that they are very effective for sensing dew (moisture).

Figure 3:
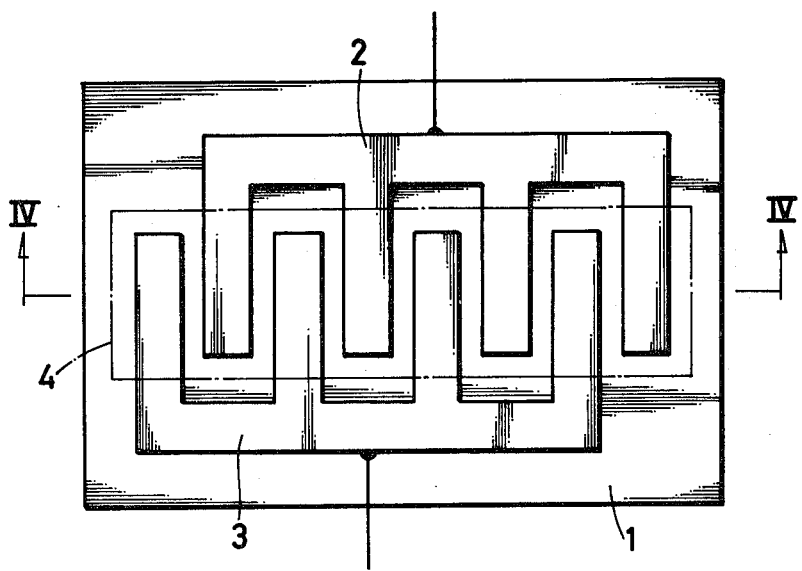
FIG. 3 is a plan view of dew-sensing hygrometer constructed in accordance with the principles of the invention.
Figure 4:
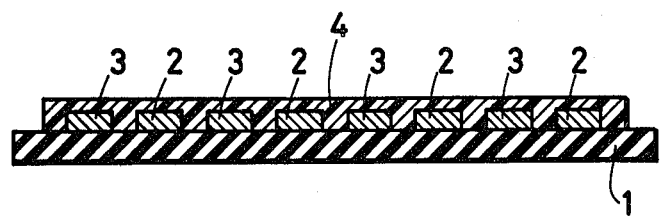
FIG. 4 is an elevated cross-sectional view, taken along the line IV—IV of FIG. 3.

Next, an exemplary embodiment of a dew-sensing hygrometer having a hygroscopic film produced in accordance with the invention will be described with reference to FIG. 3 and FIG. 4.

A dew-sensing hygrometer constructed in accordance with the principles of the invention is comprised of a base plate 1, for example, composed of a polyethylene terephthalate film (available under the registered trademark "Mylar") or composed of a glass, a pair of comb-like electrodes 2 and 3 fixed onto the base plate 1 in such a manner that teeth elements of the comb-like electrodes 2 and 3 are alternatively arranged as shown, and a dew-sensing hygroscopic film, shown by the dot-dash line, is positioned to cover at least a portion of the teeth elements of the comb-like electrodes 2 and 3. For example, when such a hygrometer is attached to the circumferential surface of a head drum of a VTR (not shown), it is preferable that the base plate 1 be formed of a flexible material. However, the base plate 1 may be made of a rigid material, as desired. The electrodes 2 and 3 may, for example, be composed of stainless steel. The thickness of the dew-sensing hygroscopic film 4 may be in the range of 2 to 9μ.

The above-described hygrometer can be very easily manufactured in comparison with the conventional hygrometer and an exemplary manufacturing process useful in constructing dew-sensing hygrometers of the invention is set forth below.

Figure 5A:
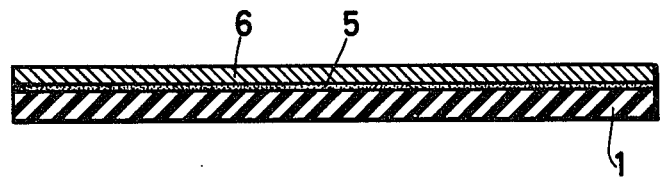
FIG. 5A is an elevated cross-sectional view of a base plate and an electrode attached to the base plate useful in the manufacture of the dew-sensing hygrometer in accordance with the principles of the invention.

As shown on FIG. 5A, a metal layer 6, for example, composed of stainless steel, is attached to the base plate 1 via an adhesive 5. Stainless steel is a preferable material for the electrodes, since such metal is resistant to rust.

Figure 5B:
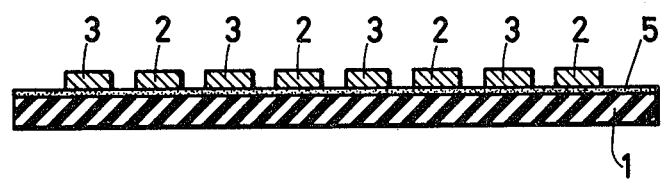
FIG. 5B is an elevated cross-sectional view of a base plate and electrode elements attached to the base plate useful in the manufacture of the dew-sensing hygrometer in accordance with the principles of the invention.

As shown on FIG. 5B, the metal layer 6 is then etched in a predetermined pattern to form the electrodes 2 and 3. A dew-sensing hygroscopic material, containing the above described organic electrolyte and polyvinyl alcohol having a saponification equivalent or degree of 20 to 65 as a base material, is coated on the electrodes 2 and 3 and surface areas of the base plate 1 between the electrodes 2 and 3 so as to form the hygroscopic film 4 having a thickness of less than 10μ, as shown on FIG. 4, by a roller method or a dipping method or any other desired coating method.

Next, the hygroscopic film 4 is heated at a predetermined temperature to vaporize any solvent (i.e. an organic solvent, such as methanol or a mixture of an organic solvent and water) in the hygroscopic film 4. In this manner, the dew-sensing hygrometer shown on FIG. 4 is obtained. In FIG. 4, the adhesive 5 is not shown.

In the above-described manufacturing process, since the solvent for the low saponification equivalent polyvinyl alcohol is an organic solvent or mixture of an organic solvent and water, the hygroscopic film 4 readily unites with the adhesive 5 when it is coated on the base plate surface areas between the electrodes 2 and 3, shown on FIG. 5B. There is no need for the viscosity of the hygroscopic material (i.e. low saponification equivalent PVA), to be as high as that of the conventional hygroscopic material and there is no need for the coated film of such hygroscopic material to be as thick as that of the conventional hygroscopic material. Even when the hygroscopic film 4 is thin, the adherence of such a hygroscopic film to the base plate 1 is very satisfactory. Since the hygroscopic film 4 can be very thin (2 to 9μ in the exemplary embodiments discussed), the diffusion path or distance of absorbed water within such a thin film is shortened and therefore a material improvement in response time is attained.

A solvent consisting only of an organic solvent can be used for polyvinyl alcohol having a low saponification degree or equivalent, since such polyvinyl alcohol is more oleophilic. Accordingly, the hygroscopic material of the invention, comprising polyvinyl alcohol having a low (20 to 65) saponification degree is easier to unite with an adhesive such as 5, and the hygroscopic film 4 can be thinner and the response time can be considerably shortened.

The dew-sensing hygroscopic element according to the invention can be produced by a simple process in which the solvent is merely vaporized by heating the hygroscopic material, after coating. In contrast to the manufacture of the conventional hygroscopic element, the photo-cross-linked process or chemical treatment process and the after-curing process can be omitted in the manufacture of the hygroscopic elements produced in accordance with this invention. Accordingly, the manufacturing process is greatly simplified. Moreover, since materials used for this invention are of low toxicity, there is no serious problem of pollution.

As above described, the hygroscopic film produced in accordance with the invention comprises polyvinyl alcohol having a low or relatively low saponification equivalent or degree (20 to 65) as a base material, and contains an organic electrolyte. Such polyvinyl alcohol base materials and organic electrolytes are very stable to water, and do not dissolve in water. The hygroscopic film produced in accordance with the invention is resistive to water and stable in water. Accordingly, it is very useful for sensing dew. For example, it is very useful in apparatus for preventing the formation of dew on the head drum of VTR or on a window of an automobile.

Further, the diffusion rate of water into the hygroscopic film of the invention is high and therefore the response time is short, in comparison with the conventional hygroscopic cross-linked or polymerized films. Moreover, since the solvent for a polyvinyl alcohol having a low saponification degree is an organic solvent or a mixture of an organic solvent and water, the hygroscopic material of the invention is easy to unite with an adhesive, so it can be coated as a relatively thin layer on the base plate. A corresponding decrease in the response time can then be attained.

This invention provides a dew-sensing hygroscopic element which does not always require a strict linear relation between the humidity-electrical resistance characteristic, as required with conventional hygroscopic element. The dew-sensing hygroscopic element of the invention can be simply manufactured whereby a polyvinyl alcohol having a low saponification degree and containing an organic electrolyte is coated on a base plate and then the solvent is removed from the coated film. Substantially more complex processes are required to produce conventional hygroscopic cross-linked or polymerized elements. With the invention there is no fear of public pollution.

While preferred embodiments have been described, variations thereto will occur to those skilled in the art which are within the scope of the present inventive concepts, which are delineated by the following claims.

What is claimed is:

1. In a dew-sensing hygroscopic element including a pair of electrodes and a dew-sensing hygroscopic material arranged between said electrodes for detecting dew with the change of impedance between said electrodes, the improvement comprising wherein said dew-sensing hygroscopic material comprises polyvinyl alcohol having a saponification equivalent raging from 20 to 65 as a base material and containing therein an amount of an organic electrolyte in the range of $6 \times 10^{-4}$ to 0.14 gram equivalent based on 100 grams of said dew-sensing hygroscopic material.

2. In a dew-sensing hygroscopic element as defined in claim 1, wherein said organic electrolyte is a metallic salt of a $C_1$ to $C_{20}$ organic acid.

3. In a dew-sensing hygroscopic element as defined in claim 2 wherein said organic acid is $C_1$ to $C_5$ of fatty acid.

4. In a dew-sensing hygroscopic element as defined in claim 2, wherein a cation of said metallic salt of organic acid is an alkali metal.

5. In a dew-sensing hygroscopic element as defined in claim 1, wherein said polyvinyl alcohol has a mean polymerization degree in the range of 200 to 3000.

6. In a dew-sensing hygroscopic element as defined in claim 1, wherein said dew-sensing hygroscopic material is in the form of film having a thickness less than $10\mu$.

7. In a dew-sensing hygroscopic element as defined in claim 6 wherein said film has a thickness in the range of about 2 to $9\mu$.

* * * * *